US00PP17222P2

(12) United States Plant Patent
Stahlhut

(10) Patent No.: US PP17,222 P2
(45) Date of Patent: Nov. 21, 2006

(54) CARNATION PLANT NAMED 'CFPC JADE'

(50) Latin Name: *Dianthus caryophyllus*
Varietal Denomination: CFPC Jade

(75) Inventor: Roy Stahlhut, Watsonville, CA (US)

(73) Assignee: California Florida Plant Company, Salinas, CA (US)

( * ) Notice: Subject to any disclaimer, the term of this patent is extended or adjusted under 35 U.S.C. 154(b) by 38 days.

(21) Appl. No.: 11/177,887

(22) Filed: Jul. 8, 2005

(51) Int. Cl.
*A01H 5/00* (2006.01)

(52) U.S. Cl. ..... Plt./273

(58) Field of Classification Search ..... Plt./273
See application file for complete search history.

*Primary Examiner*—Kent Bell
*Assistant Examiner*—Annette H Para
(74) *Attorney, Agent, or Firm*—Winston & Strawn, LLP

(57) ABSTRACT

A new variety of carnation plant named 'CFPC Jade' having large size flowers with a distinctive green color.

1 Drawing Sheet

Latin name of the genus and species: Botanical classification: *Dianthus caryophyllus.*

Variety denomination: The new carnation variety denomination is 'CFPC Jade'.

BACKGROUND OF THE INVENTION

The present invention comprises a new and distinct cultivar of hybrid carnation botanically known as *Dianthus caryophyllus*, and referred to by the cultivar name 'CFPC Jade'.

'CFPC Jade', identified as selection no. 030201, originated from a cross made by Roy Stahlhut in a controlled breeding program in Salinas, Calif. The female parent of the new variety is the unpatented variety known as selection no. 195-2 and the male parent is the unpatented variety known as selection no. 195-8. The new variety 'CFPC Jade' has been asexually reproduced by vegetative side shoot cuttings in Salinas, Calif. and the distinguishing characteristics are retained through successive generations of asexual reproduction.

BRIEF SUMMARY OF THE INVENTION

'CFPC Jade' is a potted spray-type of carnation plant variety having large size flowers with a distinctive green color.

COMPARISON WITH FEMALE PARENT

Plants of the new carnation variety 'CFPC Jade' are similar to plants of the female parent selection no. 195-2 in plant habit and growth rate. In side-by-side comparisons in Salinas, Calif., under commercial practice, plants of the new carnation variety 'CFPC Jade' differed from plants of the female parent in at least the following characteristic:

1. The new variety 'CFPC Jade' produces pure green flowers while the female parent produces pale green flowers.

COMPARISON WITH MALE PARENT

Plants of the new carnation variety 'CFPC Jade' are similar to plants of the male parent selection no. 195-8 in plant habit and growth rate. In side-by-side comparisons in Salinas, Calif., under commercial practice, plants of the new carnation variety 'CFPC Jade' differed from plants of the male parent in at least the following characteristic:

1. The new variety 'CFPC Jade' produces pure green flowers while the male parent produces pale green flowers.

BRIEF DESCRIPTION OF ILLUSTRATION

Typical specimens of the plant and flowers for the new carnation variety 'CFPC Jade' are shown in the accompanying photograph. The colors shown are as true as possible within the usual limits of this kind of illustration.

FIG. 1 is a whole plant view of the new variety 'CFPC Jade' grown in a pot. The plant shown in the illustration is 101 days from date of planting.

DETAILED BOTANICAL DESCRIPTION

The following description of the new carnation variety 'CFPC Jade' is of plants 101 days from the date of planting grown in a commercial greenhouse in Salinas, Calif. in the month of December. The cultivar has not been observed under all possible environmental conditions. The phenotype may vary significantly with variations in the environment such as temperature, length of day and light intensity without any variance in genotype.

Plants of the new variety have been grown successfully under temperature conditions averaging about 18° C. at night and about 24° C. to 28° C. during the day under light conditions of about 12 hours. Plants are daylight neutral and flower throughout the year. Chemical growth regulators are not required for production.

The new variety may be produced as a potted spray-type carnation. To produce a commercial product the plants may be pinched once with the center bud removed. Pinched plants are about 17.1 cm tall and about 17.8 cm in diameter. Flower diameter averages about 5.1 cm with a crown of about 1.9 cm. Foliage is generally about 9.6 cm long and about 0.9 cm at the widest point. The typical container size for commercial growth is 4½ inches. It has been observed that the shelf life of the new variety is about 21 days with the first appearance of color in the buds occurring at about 100–110 days after planting of cuttings. The commercial classification of the new carnation variety is a potted spray-type.

The following description is with respect to a plant produced as a potted spray-type. The plant and flower measurements and foliage size are established as an average using standard commercial cultural practices. In the description of this new carnation variety, color values have been taken from The Royal Horticultural Society Colour Chart (R.H.S.C.C.).

PLANT

Height (cm): 17.1.
Form: Herbaceous.
Growing habit: Semi-upright.
Branching characteristics: 3–4 laterals per stem.
Breaking action: 5–6 breaks per plant with strong straight stems.
First appearance of color in buds: 100–110 days after planting.
Vigor: Very good.
Shelf life: 21 days.
Blooming habit: Spray type.
Blooming season: Year round.
Lastingness of blooms: About 10 days.
Disease (susceptibility/resistance observed): Good resistance to soil-borne diseases such as *Fusarium oxysporum* and *F. graminearium*, and root rots such as damping off, water molds and similar types, as is typical of carnations.
Pest (susceptibility/resistance observed): None observed.
Drought and temperature (susceptibility/resistance observed): None observed.
Mutation prone: No.
Propagation:
*Type.*—Side shoot cuttings.
*Time to rooting.*—18 days with soil temperatures of 18° C. to 21° C.
*Rooting habit.*—Good fibrous system.
Growth treatments or special conditions: None.

FOLIAGE

Stem:
*Diameter.*—Base (cm): 0.6. Apex (cm): 0.2.
*Texture.*—Smooth.
*Cross section.*—Edged.
*Color.*—Internode: 147D. Node: 145C.
Number of leaves per lateral branch.—14–16.
Arrangement of leaves: Bi-lateral along the stem.
*Shape of leaf.*—Long, narrow, lanceolate.
*Size of leaf.*—Width (cm): 0.9. Length (cm): 9.6.
*Leaf apex: Acute.*
*Edge.*—Smooth.
*Surface texture.*—Top: smooth. Bottom: smooth.
Leaf venation: Prominent mid-vein at underside.
Leaf longitudinal axis: Recurved.
Leaf cross section (upper side): Concave.
Leaf color:
*Mature leaf, upper side.*—147A. Under side: 137A.
*Young leaf, upper side.*—147A. Under side: 137A.
Leaf waxy layer: Medium.

FLOWER

Flower appearance: Matte.
Flower type: Double.
Flower profile of upper part of corolla: Convex.
Flower profile of lower part of corolla: Flat.
Flower shape: Dome shaped, round.
Number of blossoms per branch: 5–7.
*Depth of fully expanded blossoms (cm).*—1.9.
*Diameter of fully expanded blossoms (cm).*—5.1.
Calyx:
*Sepals number.*—5.
*Length (cm).*—0.8.
*Width (cm).*—0.6.
*Color.*—Outer side: 144A. Inner side: 138D.
*Texture.*—Smooth.
*Appearance.*—Matte.
*Shape.*—Cylindrical.
Flower petals:
*Form/shape.*—Fan shaped.
*Petal edge.*—Smooth.
*Texture.*—Smooth.
*Appearance.*—Matte.
*Petal surface of blade.*—Undulating.
*Number per flower.*—30.
*Outer petals.*—Length (cm): 4.2. Width (cm): 3.5.
*Inner petals.*—Length (cm): 3.9. Width (cm): 1.8.
Fragrance: Slightly spicy.
Flower bud (at onset of color):
*Length (cm).*—2.5.
*Diameter (cm).*—1.3.
*Form/shape.*—Ovoid.
Flower color:
*1. General tonality.*—Green.
*2. Petals, upper surface.*—145B.
*3. Petals, lower surface.*—145B.
*4. Petals, edge.*—145B.
*5. Petals, center.*—144B.
*6. Early bud.*—145B.
Petal macule: Absent.
Flower progression with age: Color remains fairly constant.

REPRODUCTIVE ORGANS

Gynoecium: Pistillate.
*Pistil number.*—1.
*Pistil length (cm).*—3.0.
*Pistil color.*—155A.
*Stigma number.*—2 and 3.
*Stigma color.*—White or cream.
*Stigma shape.*—Filamentous.
*Style color.*—Whiter than 155D.
*Style number.*—2 and 3.
Ovary:
*Shape.*—Ovoid.
*Surface.*—Smooth.
*Color.*—Base: 145D. Body: 145B. Apex: 145B.
Androecium: None produced.
Fruit and seeds: None produced.

What is claim is:

1. A new and distinct variety of carnation plant, substantially as described and illustrated herein.

* * * * *

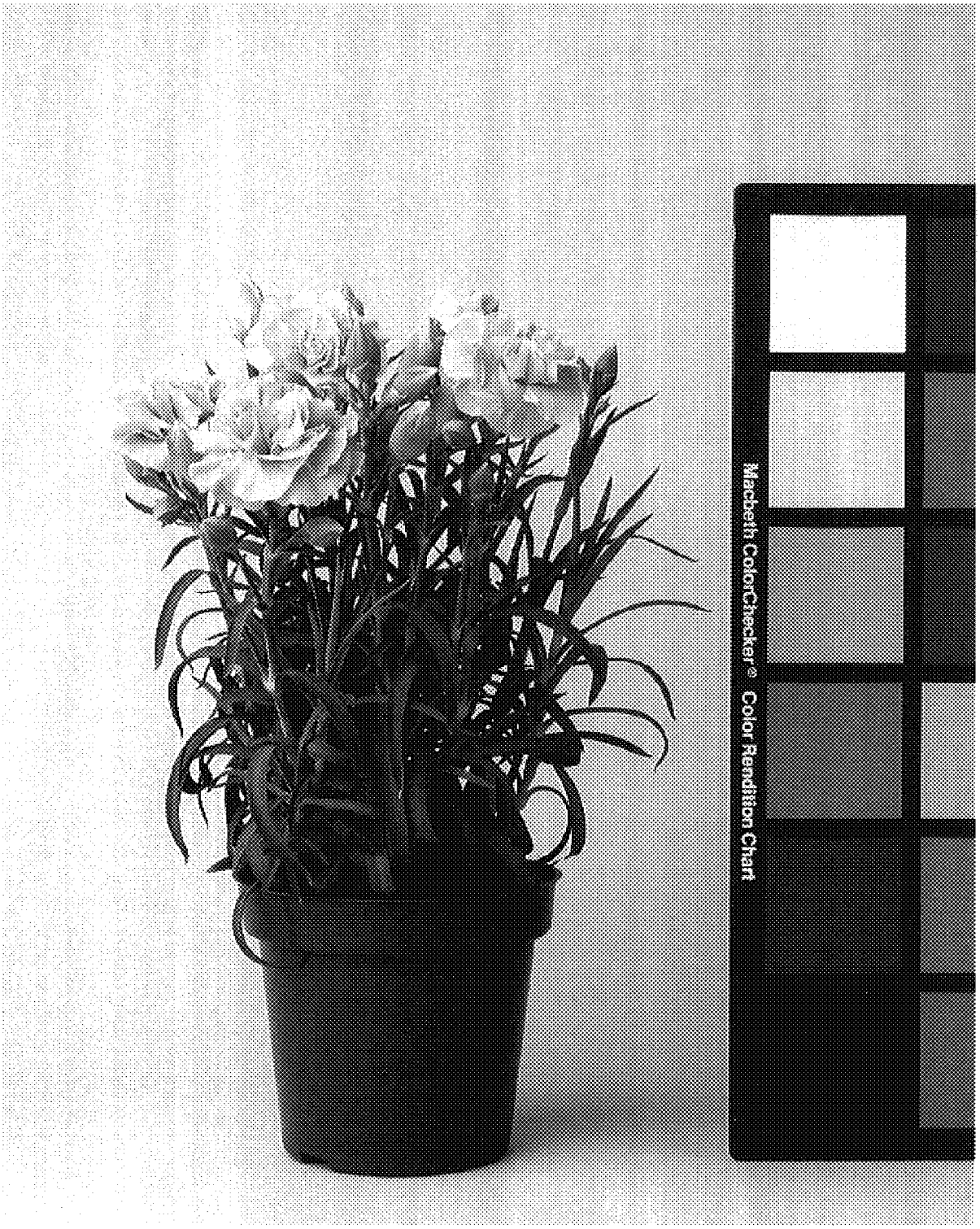
Color Rendition Chart
Macbeth ColorChecker®